(12) United States Patent
Lejeune

(10) Patent No.: US 6,777,228 B2
(45) Date of Patent: Aug. 17, 2004

(54) SYSTEM, METHOD AND APPARATUS FOR THE RAPID DETECTION AND ANALYSIS OF AIRBORNE BIOLOGICAL AGENTS

(75) Inventor: Peter Lejeune, Falls Village, CT (US)

(73) Assignee: Lockheed Martin Corporation, Bethesda, MD (US)

( * ) Notice: Subject to any disclaimer, the term of this patent is extended or adjusted under 35 U.S.C. 154(b) by 106 days.

(21) Appl. No.: 10/025,882

(22) Filed: Dec. 26, 2001

(65) Prior Publication Data

US 2004/0043443 A1 Mar. 4, 2004

Related U.S. Application Data

(63) Continuation-in-part of application No. 09/707,937, filed on Nov. 8, 2000, now abandoned.
(60) Provisional application No. 60/164,251, filed on Nov. 8, 1999.

(51) Int. Cl.$^7$ ................................................ C12M 1/26
(52) U.S. Cl. ........................ 435/309.1; 435/288.6; 73/863.23
(58) Field of Search ..................... 73/31.01, 31.02, 73/863.21, 863.22, 863.23; 356/335, 336, 337, 437; 435/288.6, 288.7, 309.1

(56) References Cited

U.S. PATENT DOCUMENTS

| 4,113,434 | A | * | 9/1978 | Tanaka et al. ............ 73/863.55 |
| 4,850,268 | A | | 7/1989 | Saito |
| 5,004,483 | A | | 4/1991 | Eller |
| 5,090,257 | A | * | 2/1992 | Bruce ....................... 73/863.03 |
| 5,164,604 | A | * | 11/1992 | Blair et al. ................. 250/574 |
| 5,200,313 | A | | 4/1993 | Carrico |
| 5,421,214 | A | * | 6/1995 | Burgdorfer .............. 73/863.22 |
| 5,500,369 | A | * | 3/1996 | Kiplinger ................. 435/309.1 |
| 5,687,093 | A | | 11/1997 | Long |
| 5,711,916 | A | | 1/1998 | Riggs |
| 5,760,314 | A | * | 6/1998 | Bromberg et al. ........ 73/863.21 |
| 5,854,431 | A | * | 12/1998 | Linker et al. ............ 73/863.23 |
| 5,904,752 | A | | 5/1999 | Willeke |
| 6,051,189 | A | | 4/2000 | Wick |
| 6,584,865 | B1 | * | 7/2003 | Doherty et al. .......... 73/863.03 |

OTHER PUBLICATIONS

K. Bradley et al, "Identification of the Cellular Receptor for Anthrax Toxin," Nature, vol. 414, Nov. 8, 2001.

* cited by examiner

Primary Examiner—David A. Redding
(74) Attorney, Agent, or Firm—Andrew C. Aitken; Venable, Baetjer, Howard and Civiletti LLP

(57) ABSTRACT

A sampling device for detecting airborne particles has two parallel substantially identical intake passages. Each intake passage, in close proximity to the other, and has an inlet, a sampling filter intersecting the passage, means for drawing ambient air through the inlet, and sampling filter. The sampling filter is mounted on a filter magazine that has a plurality of sampling filters. A motor is provided for sequentially moving successive sampling filters on the magazine into the air flow. The sampling device accordingly captures two substantially identical samples from the parallel intake passages.

5 Claims, 2 Drawing Sheets

SYSTEM, METHOD AND APPARATUS FOR THE RAPID DETECTION AND ANALYSIS OF AIRBORNE BIOLOGICAL AGENTS

The applicant claims the benefit of the filing date of U.S. application Ser. No. 60/164,251, filed Nov. 8, 1999, and is a continuation-in-part of U.S. application Ser. No. 09/707,937 filed Nov. 8, 2000 now abandoned.

FIELD OF THE INVENTION

The invention relates to the field of airborne biological pathogen detection. More specifically the invention is directed to a sampling device and particle detector for the detection of air borne particles that have sizes consistent with certain hazardous biological pathogens that can be used as biological warfare agents. The invention also relates to a integrated system of sampling devices described herein that is useful for the detection of potential airborne biological pathogens.

BACKGROUND OF THE INVENTION

There is a concern among public officials in the United States that certain populations when grouped in large numbers or while attending public events are vulnerable to terrorist attack and, more particularly, vulnerable to attack by the use of air borne biological and chemical agents. For example, events of concern include civic events such as parades, national and local celebrations, sporting events, marches and political rallies that involve the gathering of large numbers of individuals. A further concern among public health officials is the dispersal of such agents in a large indoor environment such as subway systems, indoor arenas, shopping malls, office buildings and large banquet facilities. A further concern among both public heath and security officials is the targeted release of biological agents in the proximity of certain government buildings such as, the FBI, the Pentagon, the White House, the Capitol, or military installations and naval vessels. Any of these locations make attractive targets for terrorists and the costs associated with installing and monitoring detection devices in such targeted geographical regions may be justified by the threat.

Although effective delivery methods for airborne biological agents remain a logistical problem for terrorists, a number of delivery methods are considered viable. Currently, anticipated manners to deliver such biological agents into the air include aerosols from either aircraft or ground based mobile systems. It is generally acknowledged that to be an effective biological weapon, airborne pathogens must be dispersed as fine-particles between 1–20 microns and preferably, between 1 and 5 microns in size. Infection with aerosolized or lyophilized agents like *Bacillus anthraces*, small pox, brucellosis, tularemia, and Venezuelan Equine Encephalitis ("VEE"), usually requires deep inspiration of infectious dose, best achieved by small particle size of about 1 to 5 microns. The aerosolized delivery of biological agents can be achieved by rather "low-tech" aerosolization methods including agricultural crop-dusters; aerosol generators on small boats, trucks, or cars; backpack sprayers; and even hand size atomizers, such as those used for perfume applications.

Because biological attacks typically do not manifest symptoms until some time after the first exposure of the virulent agent, an early and accurate identification of the agent is of critical importance. The rapid identification of the agent may allow authorities to quickly implement a measured remedial response, which may involve a range of actions including evacuations, quarantines, educational and information campaigns, and the administration of medical treatment. Early detection of a biological agent in the environment allows for early specific treatment and time during which prophylaxis would be effective. The ability to accurately detect the presence of such agents without false positives is particularly important to the public health of civilians and government officials. An early, rapid and accurate detection is also a paramount concern among law enforcement officials. If such law enforcement offices quickly perceive and understand that a biological attack is underway, the chances of apprehending the perpetrators is also increased.

SUMMARY OF THE INVENTION

The present invention involves a sampling and detection device for airborne particles that includes a dual air intake and filtering system for the parallel sampling of ambient air. Air first flows past a particle detectors that provide a signal in response to the presence and size of particles entrained in the air. The particle detectors are calibrated to be particularly sensitive to those signals. In a preferred embodiment the particle detector comprises a LED and photodetector array that detects the presence of light that is reflected from particles entrained in the air stream. Very large particles are prevented from entering the air intake by a mesh screen. The signal from the photodetector is transmitted to a microprocessor, stored and compared to signals from known circumstances. For example, the duration and intensity of a pulse from a photodetector is indicative of the respective size of the particle. In the event that the signal from the microprocessor is similar to a known signal, the microprocessor will implement a communications program that will cause the data to be transmitted over a wireless link. In an alternative embodiment the microprocessor will process the signal and seek a predetermined increase in the signal strength and from a baseline. In the event that the threshold is surpassed, the communications program is implemented and the data from the storage is communicated over a transmission link. The sampling stations contain two parallel filters across the downstream of the particle detectors for the capture of particles. A plurality of filters are provided at the location and the filters are automatically sequentially introduced into the airstream at predetermined time intervals. As filters are removed from the airstream they are sealed, secured and labeled with the time and other information relating to the location of the sample.

In a preferred embodiment of the invention, in addition to the data relating to particle size, additional information is also that identifies the sampling station, the location of the station, ambient weather condition and the time that the data was recorded. Thus in a preferred embodiment the sampling station includes a global positioning system, a clock, weather monitoring equipment. Data from each of these components is transmitted to a remote location.

In yet a further embodiment a number of sampling devices in a particular geographic locations are continuously monitored from a remote location. Data may be automatically transmitted at predetermined time intervals, regardless of the input from the photodetector and read by a technician. Thus data is transmitted to a remote command unit location for analysis and processing. For example the data from the photodetector can be correlated with wind speed and the time of the sample. Later, either at predetermined time intervals, or, for example, in response to a signal from the processor that indicated that the photodetector signal exceeded a predetermined threshold, the filters for the corresponding time interval are collected from the sampling station and analyzed.

The invention further provides an integrated mobile system for the detection of airborne biological pathogens comprising a plurality of the aforementioned sampling devices at various geographic locations, the sampling device capable of communication, preferably by a wireless means, with a central command unit which further comprises a mobile laboratory equipped for the qualitative and rapid analysis of pre-selected target agents.

DETAILED DESCRIPTION OF THE INVENTION

Figure 1:
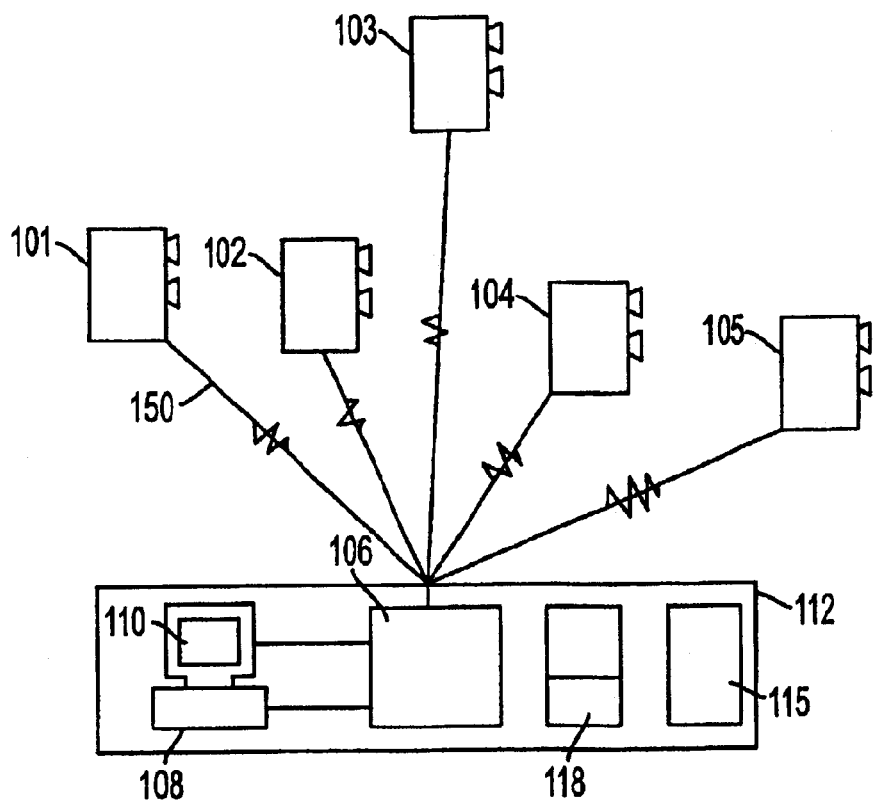
FIG. 1 is a schematic representation of the system according to the invention depicting a system of the present invention wherein a plurality of sampling devices communicate with a central command unit.

First turning to FIG. 1, which represents the integrated system according to the invention wherein a plurality of sampling devices 101–105 (the depiction of five such devices is illustrative only, the invention is by no means limited to only five). The sample collectors each have at least one particle detector that is in communication via a communications link 150 which transmits data relating to particle size collected by the particle detector to a central command unit 106. The central command unit is preferably a mobile vehicle like a trailer, truck, or recreational vehicle and must be large enough to house a mobile laboratory.

Figure 2:
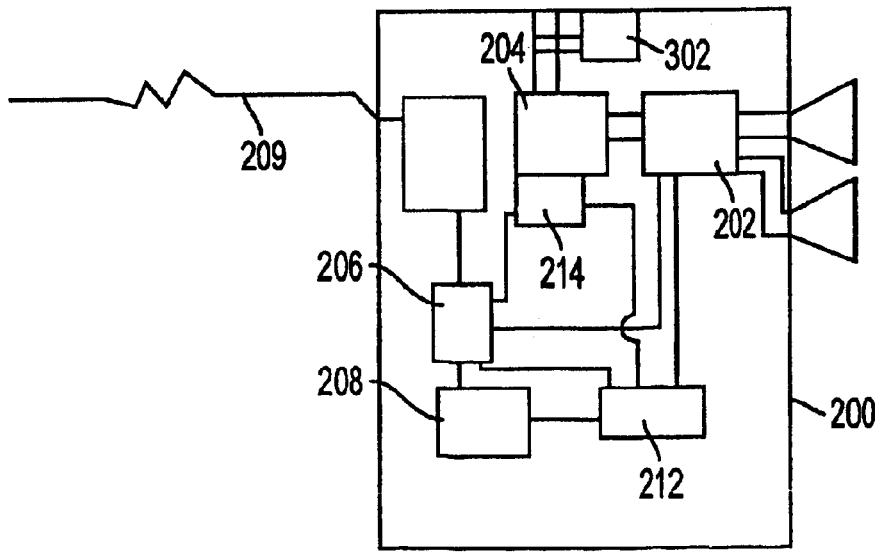
FIG. 2 is a schematic representation of a sampling device according to a preferred embodiment of the invention.
Figure 3:
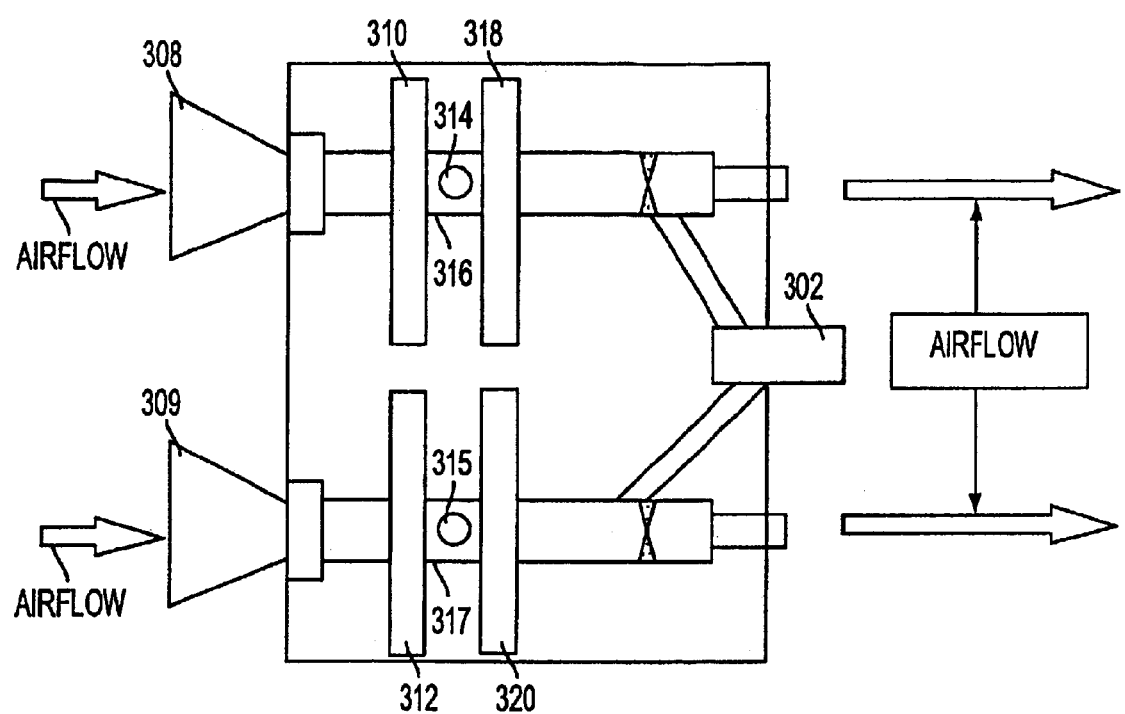
FIG. 3 is a schematic representation of the dual air sampling device according to a preferred embodiment of the invention.

The sampling device is more particularly illustrated in FIGS. 2 and 3. Now referring to FIG. 3, the schematic representation shows the sampling device comprised of a dual air filtering sampling system according to the invention. The sampling device employs a dual array of both sampling and screening filters. The sample filters are positioned on a magazine and rotated in front of an air-sampling device for predetermined time intervals. Ambient air is drawn into the respective sampling station through an inlet collector 308 and 309 by motor driven vacuum pump 302. Upon the elapse of the predetermined time interval, the filters are removed from the respective magazine and correlated with other sampling data such as the time the sample was taken; reported by a time signature from an included clock (not shown), the location of the sampling station optionally determined by a global positioning system, and some arbitrarily assigned sampling station identification. Although the filters are described to be on a rotating magazine, in an alternative embodiment the sample filters could be aligned in a linear arrangement and each filter sequentially passed by the air stream. The sample filters 318 and 320 which uptake particles from the ambient air, are then subsequently transported for qualitative analysis along with their correlated time and place data. After a sampling interval has elapsed, the sample filter 318 is removed from the sample stream, removed from the magazine, and then sealed in an airtight packaging. In a preferred embodiment the controller (FIG. 2, 206) located at each respective sampling station is programmed to print and have applied a pressure-sensitive adhesive label that contains sampling information. Information relating to the geographic location may be accessed from a Global Positioning System (FIG. 2, 208). The pressure-sensitive adhesive label is applied to the exterior of the filter canister or packaging. The correlation of such sampling information with the sample enables the operator of the integrated mobile system to subsequently plot a plume of the biological pathogens dispersed and to determine its characteristics. Information relating to weather conditions at the sample device location such as wind speed and direction can also be used to map the plume and determine potential human exposure. Such sampling information may be used in connection with both remedial efforts and law enforcement investigation. For example, analysis of sampling data from multiple sampling stations may reflect that the origin of a plume of an airborne biological agent is from a point source or a line source, indicating that the source of the biological agent is moving, such as from a vehicle. For example, in weather conditions having a prevailing winds in a single vector, data—such as concentration of contaminant and time of collection—, from an array of sampling stations also arranged in a linear relationship can provide information on the source and direction of travel of the contaminant source.

An automated system for removal of filter canisters from a filter magazine without handling is preferred because it serves to minimize both the potential of adverse contamination to the collection technician and maintains the integrity of the sample by reducing handling error.

As depicted in FIG. 3, a preferred embodiment of the dual air collection system for the sampling of potential airborne pathogens is provided. A motor driven vacuum pump 302 draws air through intake manifolds 308 and 309, and through a first pair of parallel screening filter elements 310 and 312 for a predetermined time. The intake manifolds are preferably sufficiently proximal (no more than 5 yards apart) so as to provide each intake manifold with the same sampling environment and limit variability between samples from the same device. While a first sample is available for immediate quantitative analysis the second sample is may be retained for archival purposes.

This first pair of screening filter elements 310 and 312 remove large particulate matter (greater than about 20 microns) generally not characteristic of particles in the size range of biological pathogens. Downstream of the screening filter elements 310 and 312 are particle detectors 314 and 3 15 which provide an output that reflects the number of particles in the targeted range within flow cells 316 and 317 respectfully. According to the invention, the targeted range for such particles is about 0.5 to about 20 microns. Particles in this range are capable of pathogenic activity due to inhalation. Immediately downstream of flow cell 315 and 316 are dual sampling filters 318 and 320. Sampling filters 318 and 320 represent filters within a sampling filter magazine that comprise a plurality of separate filters. These filters are sized with a porosity capable of capturing particles of about 0.5–20 microns. Upon the elapse of a predetermined time, both pairs of the screening filters and sampling filters are removed from the air stream and new filters are replaced within the stream. The screening filters must be periodically changed to ensure that air-flow through the sampling station remains constant. One such filter may serve as a control sampling filter; filter 318, and is transferred to an offsite laboratory. The second sampling filter element 320 is intended to be immediately transferred to the central command unit 112 (FIG. 1) for field-testing and analysis. In this regard, the command and control unit 112 is preferably outfitted as a mobile laboratory equipped to test and detect the presence of potential pathogenic biological agents, infra.

Particle Detectors of the Invention

Particle detectors fall into four general categories: filtration, inertial & gravitation, and optical & electrical mobility. Most methods require isokinetic sampling, usually accomplished using sharp edged probes and suction pumps. Sampling points must also be chosen a sufficient distance away from disturbances (or system effects).

In the preferred embodiment of the invention, the devices used to capture the sample is a s a HEPA filter. Alternative particle detectors 314 and 315 are selected from elutriations, cascade impactors, virtual impactors, cascade cyclones, real-time analyzers, or centrifugal spectrometers. As discussed above, a preferred embodiment the particle detector is comprised of a light emitting diode and a photodetector. Other particle detection methods within scope of this invention include sample detectors utilizing the following electrical mobility techniques:

Electrical aerosol analyzers (EAA) comprising unipolar diffusion chargers, a mobility analyzers and detectors. Particles acquire electrostatic charge, pass through the analyzer and then collect at the detector filter where the charge drains to ground. This analysis is ultra sensitive and allows the discrimination of particles in the range of 0.013 to 0.75 microns.

Differential Mobility Analyzers (DMAs) work on similar principles but have an electrostatic classifier in place of the mobility analyzer. Particle detection ranges for these analyzers are in the range of 0.01 to 0.9 microns.

The LIDAR System (Light Detection And Ranging) uses light waves in the same way that radar uses radio waves. A laser shoots a beam of coherent fight at a specific frequency at some target. The light which is back-scattered from objects, including molecules and bioaerosols, is received by mirrors and analyzed, again similar to the way radar signals are interpreted.

Filters Useful Sampling Devices Invention

The filter magazine contains a plurality of sample filters periodically changed so that samples can be collected and to insure accurate sample detection without over-saturating existing filters. New sample filters contained on the magazine are inserted within the sample stream at predetermined intervals. A conventional High Efficiency Particulate Air Filter (HEPA) filter is preferred, which filter HEPA comprises a continuous sheet of a special paper-like, glass-fiber filter medium is pleated into a "v" configuration with corrugated aluminum separators between the pleats. This "v" configuration forms the filter elements. The filter element is then bonded into a rigid frame using a special polyurethane compound. Standard filters are produced in a range of face dimensions and in two standard depths of about 150 mm and 300 mm. Another type of construction is used for "minipleat" filters, which are produced in depths down to 50 mm. They have very close pleating of the filter medium, and manufacturers use various separation techniques to create minimal spacing between the pleats. The Ultra Low Penetration Air (ULPA) filter, a filter developed for microelectronics clean-rooms, is also useful. This filter uses a higher-efficiency medium and has much higher pressure drop than normal HEPAs.

In an alternative embodiment, a cascade impactors cam be used to collect samples. These devices work by directing laminar airflow into and around a series of impact plates. The air velocity increases at every stage such that large particles are deposited in the first stage and successively smaller particles are collected through the remaining plates. The final stage usually contains a submicron filter. The size range for both cascade and virtual impactors, infra, is about 0.08 to 35 microns.

Reporting Particle Sample Data Central Command Unit

Upon determining the presence of particles in the size range that is indicative of the presence of airborne biological pathogens. The sampling device transmits the data via the communication link 105 (FIG. 1) which can be any of the following interfaces known in the art that include without limitation; Cat5e cabling, serial interface cabling, Small Computer Systems Interface (SCSI), Coax cabling, Parallel cabling, IEEE cabling, fiber optic, Cray cabling, telephone analog cabling, ISDN cabling. In the preferred embodiment the communication link 105 is achieved through wireless communications.

Wireless communications may be achieved through the inclusion of processors embedded with wireless logic protocols including without limitation the Bluetooth and WAP protocols. These protocols enable the communication link to transmit data in computer readable format to the central command unit. Data such as location, time, and weather conditions are transmitted and thus correlated with the samples obtained. Devices which transmit wireless data and the antennas required for wireless communication are known to those skilled in the art and can be readily integrated to into the sampling devices to transmit any data generated without undue experimentation. Such systems, method protocols, and devices include U.S. Pat. No. 6,330,454, System and method for locating mobile units operating within a wireless communication system, U.S. Pat. No. 6,330,447, Method for maintaining reliable communication in a wireless communication system, U.S. Pat. No. 6,324,564, Optimized wireless communication system, U.S. Pat. No. 6,329,948, Method of determining position of wireless communication terminal, U.S. Pat. No. 6,240,126 and U.S. Pat. No. 6,208,876, Wireless communication device, U.S. Pat. No. 6,131,040, Wireless communication device receiving configuration data from multiple sources, U.S. Pat. No. 5,914,689, Antenna for a portable, wireless communication device, and U.S. Pat. No. 5,739,792, Wireless communication device with electrical contacts, all of which are incorporated herein by reference in their entirety. Devices that are used to automatically capture data from the environment and subsequently transmit such information are well known.

The central controller is further provided with input devices such as a keyboard 108 and a monitor 10 and comprises the command and control unit 112. The command and control unit is preferably a mobile unit and contains qualitative analysis equipment 115 for the rapid identification of target biological pathogens. Preferred embodiments of the mobile command unit 112 further employ a weather monitoring station 118 that includes a vane for wind direction and a wind speed meter.

Now referring to FIG. 2 in the preferred embodiment each sampling device 200 includes at least one particle detector 202, a sample filter 204, a controller 206, a global positioning system ("GPS") 208, a communications link 209 for transmitting particle data, and a power source 212. Although any communications system can achieve the object of the invention, wireless technologies are preferred for practical considerations, especially in view of intended deployments of the system at temporary locations.

In the preferred embodiment both the particle detectors and sample collection equipment of the sampling stations are designed to operate off battery power for intervals up to twelve hours. In addition to the particle detector and the vacuum pump that draws ambient air through the sample filter, the battery pack must have sufficient power to operate the controller, the communications system and the GPS. The sampling station includes a controller 206 that provides instructions to a motor 214 (FIG. 2) to periodically rotate the filters from a magazine within the sample air stream every fifteen to thirty minutes. Air is drawn through the filters by vacuum pump 302 (FIG. 3) and the flow of air is maintained at a constant rate. The preferred maintained flow rate is preferably similar to that of human respiration in a typical adult. Because the exposure time of each filter is controlled and monitored, the sampling system would also be able to provide a rough estimate or extrapolation of the number of particles that a single individual may have been exposed to during an event and therefore the information could then be used to estimate the approximate dose delivered to the target population.

The detection of airborne or aerosolized biological agents involves two principal actions, a detection step and an identification step. In the detection step, the device is engineered to capture information relating to the number of particles in a range of about 0.5–20, preferably between about 0.5 to 5 microns (this size particle is most likely to settle in the alveoli and manifest disease), the typical range of particle sizes of concern in connection with biological pathogens. Most dust, pollen, molds, and spores are typically smaller and are in the range of 0.01 to 0.5 microns. Larger sized particles are effectively trapped by mucosae within the respiratory system and particles smaller than 0.5 microns do not readily settle within the alveoli but rather are exhaled by normal expiration. This initial particle detection step may be performed on strict quantitative or empirical basis or be based upon the relative increase in the particle count above a background count. In a preferred embodiment the particle detection is performed using an infrared light source and photo-detectors that can measure both the transmission and reflectivity of particulate materials suspended in a sample stream within a flow cell (see LIDAR system, supra). Information related to the number and size of particles is collected by the detector 202 and ultimately transmitted by the communications link 209 (equivalent to communication link 150 of FIG. 1) to the central command unit 112 (FIG. 1) for processing and analysis. For example, a light scattering method such as a particle flux monitor can measure the number and size of potential biological particles by focusing a laser beam emitted from a laser diode onto a particle detecting zone with a converging lens, scattering the laser beam when particles pass across the beam, and then collecting the scattered light by means of photodiodes.

The communications linkage 150 (FIG. 1) allows for the remote monitoring and control of a number of functions from the remote sampling stations from central command unit 112. This feature allows a coordinated analysis of a potential threat and enables the operator to quickly identify the precise location of sampling devices that can be identified for accelerated field testing based upon sensed conditions (e.g., number and size of detected particles per predetermined air sample) intelligence or a suspected adverse event. In addition to receiving input from the sample stations in the form of information relating to particle detection characteristics and location, command unit 112 can provide output commands through communication link 105 to the sampling devices such as instructions to alter the sampling interval frequency. Thus, in the event that the particle detectors within said sampling devices indicate a significant increase in the particle count of particles having the particular target size at a particular station, the operator can quickly identify the location and provide a command to increase the frequency of sampling. Operators at command unit 112 may also immediately dispatch personnel to physically retrieve filters 318 and 320 containing the samples from the sampling devices for analysis. Further, in the event of the detection of an adverse event, such as the detection of the detonation of an explosive device or identification of suspicious activity by intelligence sources, the sampling filters can be immediately retrieved for analysis.

When deployed and activated, the system will operate so that the sample collection system will run for a predetermined time intervals, typically about fifteen minute intervals. The presence of airborne particulate matter is continuously monitored. In an alternative embodiment, the sample time interval is dependent on data received from the particle counters. In the event the particle detector detects an increase in target particles or, if a biological agent is detected based upon other intelligence, such as human intelligence, the analysis of the filters may be accelerated. Data from the particle counters located at the sample devices may also be correlated with the filter that is functioning during the particular time interval so the operator or technician can determine if a particular sample was harvested at a time interval where there was a significant increase in particle count. Sensitivity of the system may be enhanced by increasing the rate of air-flow through the filters, increasing the size of the filters and by decreasing the interval periods that filters are changed.

In another embodiment, the system described herein is implemented in conjunction with ancillary services including an analysis of the threat and vulnerability to both the public and law enforcement personnel. Recommendations to minimize the threat such as restrictions on access to certain locations near the event, road closings, and restrictions such as time of day of the proposed event, would be included in the analysis. The technical analysis and review would be used to determine the optimal placement of the filters, the deployment and equipment provided in the mobile laboratory and any associated command and control functions. An operational plan regarding the location and collection of the filters would be developed based upon the nature of the event. This aspect of the invention is intended for use in the monitoring of a geographic area less than one square mile and in which the weather conditions are generally the same. As an example, the system could be deployed at new years celebrations, fourth of July celebrations and parades. The location of the sampling stations would be dependent on the wind conditions and physical features of the region such as rivers, bays and other boundary features. The sampling filter system can be integrated with the JBPDS (Joint Biological Point Detection System) and the BAWS (Biological Aerosol Warning System) to form a comprehensive detection and analysis network. Thus precise deployment of the system, including the number of sampling and detection stations, is based on the nature of the threat, the size of the event and the geographic characteristics of the targeted geographic area.

Upon removal of the filters from the collection system, a first filter is transferred to a mobile laboratory that is deployed near or at the sampling location for immediate analysis. The filters are back-washed and any particulate matter that entrapped on the filter is suspended into solution. The solubilized particles obtained from the filters are prepared for analysis by methods well known in the art. Typically, bacterial lysis solutions can be used on analytes even with low bacterial (or viral) titers to extract nucleic acid material therefrom. Sample preparation kits are widely available, for example from Qiagen® (QIAamp DNA Mini Kit). DNA extracted from solution is then be amplified with known amplification methods using predetermined primers which target certain markers of the biological agents (i.e. Polymerase Chain Reaction or derivatives thereof). In the case of *Bacillus anthraces*, the encoding nucleic acids for anthrax oedema factor, anthrax lethal factor, and for anthrax protective antigen have been isolated and marker specific primers can readily be synthesized using methods known in the art. Bradley et al., (2001) *Nature*, Volume 414 in Letters to Nature. See also, the patent to Megerle, U.S. Pat. No. 5,874,046 that is incorporated by reference herein.

Laboratory equipment (i.e., thermocyclers, test tubes, clean rooms, and refrigeration devices) used in the DNA preparation and PCR amplification procedures are housed in the mobile command unit and initial information characteristic of the threat could be at the or near the location. The invention is not limited to one type of mobile laboratory. A similar mobile laboratory useful herein is described by Saito et al, in U.S. Pat. No. 4,850,268 and is herein incorporated by reference in its entirety. Saito describes a multi-purpose laboratory room for mobile applications. The room comprises a housing structure having an airtight laboratory unit and an entrance unit, an air-conditioning and exhausting equipment unit to be installed in the upper part of the housing structure and a drain processing equipment unit to be equipped in the airtight laboratory unit. The clean levels of the laboratory unit and drain processing can be selected in multiple steps by electrical signal control. The laboratory room is comprised of a hollow wall structure, and floor and ceiling, in which air pressure in the hollow parts are controlled. The filter is provided with a heating device. In addition, an autoclave automatic sterilizing device is incorporated for processing drain. A suspension type vibration-isolating device is also equipped therein.

In a preferred embodiment, the mobile laboratory is also implemented to contain a clean room. Due to the potential severity of the biological pathogens that might be brought into the lab from the sampling device. A clean-room which is preferably compartmentalized from the rest of the mobile unit, is vacuum sealed, and further sealed off from the outside. The preferred clean-room configuration is one implemented for the manufacture of integrated circuits.

The US Federal Standard Fed-Std-209E has a well defined specification for the classification of a clean room. The specification recommends a particle count check upon the acceptance of a newly built clean room and suggests periodic checks thereafter. The industry norm is to perform an "As Built" or "At Rest" check first, and then an "On Operational" check later.

Qualitative detection of specific nucleic acid sequences from the biological pathogen can be subsequently performed, for example by using the fluorogenic 5' nuclease assay. This method involves use of a fluorogenic probe complementary to a characteristic nucleic acid target sequence that is added to the PCR reaction mixture. The probe consists of an oligonucleotide with a reporter and quencher dye attached. During the PCR process if the target sequence of interest is present, the probe anneals between the forward and reverse primer sites. The nucleolytic activity of the polymerase cleaves the probe, which results in an increase in the fluorescence intensity of the reporter dye. This process occurs in every cycle of the PCR process and does not interfere with the accumulation of PCR product. To induce fluorescence during PCR, laser light is distributed to the sample wells contained on the PCR processor using an array of optical fibers. The resulting fluorescent emission returns via the fibers and is directed to a spectrograph with a charge-coupled device (CCD) camera U.S. Pat. No. 6,322,980, Single nucleotile detection using degradation of a fluorescent sequence, U.S. Pat. No. 6,280,933, Multichromophore fluorescent probes using DNA intercalation complexes, and U.S. Pat. No. 6,268,132, Fluorescent N-nucleosides and fluorescent structural analogs of a N-nucleosides provide exemplary methods and techniques for carrying out fluorogenic 5' nuclease assay, see also Sambrook, J. et al., Molecular Cloning: A Laboratory Manual, 2nd Edition, Cold Spring Harbor Press, Cold Spring Harbor, N.Y., 1989, and Ausubel, F. M. et al. Current Protocols in Molecular Biology, Vol. 2, Wiley-Interscience, New York, all of which are incorporated by reference in their entirety.

Commercially available PCR equipment can simultaneously process multiple samples thereby allowing for the analysis of multiple antigens or agents. Qualitative analysis using the PCR process combined with nucleic acid probes is both highly specific and highly sensitive. In the event of a positive detection, an immediate and measured response can be coordinated including treatment options, educational regarding the exposure, evacuation and quarantine measure.

In an alternative embodiment the sample is subjected to involving flow cytometry. Further analysis methodologies can be enzyme immunoassays ("EIA") or rapid test technologies selected to test for specific antigens characteristic of predetermined biological agents that are a potential threat. Both conventional EIA testing and rapid test methods are engineered to allow for the presence of the target agent to be automatically detected by reflectivity at certain light wavelengths and therefore the detection of the presence of a color reflects the presence of the pathological agent or antigen.

The advantage provided by the sampling devices of the present invention provide sampling by dual filters working in parallel. The advantage of the parallel system is that the secondary filter serves as a control. The control filter 320 is transported from the sampling location to an appropriate laboratory such as a PHS laboratory or to the U.S. Army Medical Research Institution of Infectious Diseases. The secondary sample is provided both as a reference to detect the change in particles and as a repository for particles not tested that can be harvested for further evaluation.

In emergency situations when attacks by biological agents are imminent, there is little time to sort samples and determine how much the sample is necessary for evaluation and how much the sample can be kept. Due to the nature of DNA extraction used herein and the evaluation of the genotyping procedure, the bacterial or viral samples obtained from the filters are lysed (or denatured in the case of viruses) in solution and therefore destroyed. This prevents further evaluation of the sample and the availability of sample for use in evidentiary procedures or for bacteriological evaluations to determine their source. The secondary filter, therefore, provides for this previously unmet need.

Furthermore, the integrated system is deployed as a service tailored to be user specific requirements and budget. Providing the systems as a service allows municipalities and other organizations to avoid large capital expenditures on both the hardware and the trained personnel required operating and maintaining the systems. Such services could be implemented for short term events such as parades, marches, rallies civic events or be on a longer term contract basis such as the monitoring of air sample in the vicinity of a specific building or installation. Rendering of the service can also catered to the specific nature of the threat, including the geographic considerations and, the may attempt to the possible target agent.

In another embodiment, a sample collection system is provided as a mobile unit that is designed to take samples from environmental surfaces. In this embodiment a sample technician can direct the location of the air intake to specific environmental surfaces under investigation or suspicion. In a contemplated application of this embodiment, a technician may use the mobile laboratory to test for biological active agents at a particular location incident to an investigation or search.

In yet a further embodiment of the invention, the sample collection system described above is deployed within the environmental system of a building such as heating ventilation and air conditioning (HVAC) system of a particular building or aboard a ship.

What is claimed is:

1. A sampling device for detecting airborne particles comprising:

(i) two parallel substantially identically designed intake passages, each said intake passage being in close proximity to the other, and each intake passage having an inlet, (ii) a sampling filter intersecting each said passage, and (iii) means for drawing ambient air through each inlet and through said sampling filter, said sampling filter mounted onto a filter magazine, (iv) said filter magazine comprising a plurality of sampling filters, and means for sequentially moving each said sampling filter from said filter magazines into each said intake passage, and (v) wherein said sampling device can capture two substantially identical samples from said parallel intake passages.

2. The sampling device for detecting airborne particles as in claim 1 further comprising at least one particle detector, said particle detector positioned in said passage between said inlets and said sampling filter, said particle detector provide data as output reflecting the numbers and sizes of target particles.

3. The sampling device for detecting airborne particles of claim 2 further comprising a means for transmitting particle data gathered by said sampling device to a remote location.

4. The sampling device for detecting airborne particles of claim 1 wherein the communication means is a wireless communication system.

5. The sampling device for detecting airborne particles of claim 1 further comprising a global positioning system.

* * * * *